United States Patent
Giampapa

(10) Patent No.: US 8,968,801 B1
(45) Date of Patent: Mar. 3, 2015

(54) SUPPLEMENT COMPOSITION FOR SUPPORTING DNA REPAIR AND METHOD OF USE

(75) Inventor: Vincent C. Giampapa, Montclair, NJ (US)

(73) Assignee: Cellhealth Technologies Ltd., Montclair, NJ (US)

( * ) Notice: Subject to any disclaimer, the term of this patent is extended or adjusted under 35 U.S.C. 154(b) by 116 days.

(21) Appl. No.: 13/573,385

(22) Filed: Sep. 13, 2012

Related U.S. Application Data

(60) Provisional application No. 61/534,637, filed on Sep. 14, 2011.

(51) Int. Cl.
*A61K 36/282* (2006.01)
*A61K 36/74* (2006.01)
*A61K 36/31* (2006.01)
*A61K 31/05* (2006.01)
*A61K 31/465* (2006.01)
*A61K 31/6615* (2006.01)

(52) U.S. Cl.
CPC ........... *A61K 36/74* (2013.01); *A61K 31/05* (2013.01); *A61K 31/465* (2013.01); *A61K 31/6615* (2013.01); *A61K 36/282* (2013.01); *A61K 36/31* (2013.01)
USPC .............................. 424/740; 424/755; 424/725

(58) Field of Classification Search
None
See application file for complete search history.

(56) References Cited

U.S. PATENT DOCUMENTS

| | | | | |
|---|---|---|---|---|
| 5,948,808 A * | 9/1999 | Safe | ................. | 514/415 |
| 6,020,351 A * | 2/2000 | Pero | ................. | 514/355 |
| 6,361,805 B2 * | 3/2002 | Pero | ................. | 424/725 |
| 2001/0031739 A1 * | 10/2001 | Dare | ................. | 514/44 |
| 2004/0001817 A1 * | 1/2004 | Giampapa | ................. | 424/94.1 |
| 2004/0151787 A1 * | 8/2004 | Pero et al. | ................. | 424/725 |
| 2005/0196467 A1 * | 9/2005 | Giampapa | ................. | 424/641 |
| 2005/0287131 A1 * | 12/2005 | Schock | ................. | 424/94.1 |
| 2006/0269616 A1 * | 11/2006 | Giampapa | ................. | 424/641 |
| 2009/0220481 A1 * | 9/2009 | Maes et al. | ................. | 424/94.61 |
| 2010/0291190 A1 * | 11/2010 | Giampapa | ................. | 424/450 |
| 2012/0244135 A1 * | 9/2012 | Daly et al. | ................. | 424/94.1 |

OTHER PUBLICATIONS

Filing receipt and specification for patent application entitled "Dietary Supplement System for Multifunctional Anti-Aging Management and Method of Use," by Vincent C. Giampapa, filed Sep. 13, 2012 as U.S. Appl. No. 13/573,386.

Hanakahi, Les A., et la., "Binding of Inositol Phosphate to DNA-PK and Stimulation of Double-Strand Break Repair," Cell, Sep. 15, 2000, vol. 102, pp. 721-729, Cell Press.

Remington, Joseph P., et al., "Remington's Pharmaceutical Sciences," 1990, Eighteenth Edition, Mack Publishing Co.

* cited by examiner

*Primary Examiner* — Chris R Tate
(74) *Attorney, Agent, or Firm* — Conley Rose, P.C.; Jerry C. Harris, Jr.

(57) ABSTRACT

Disclosed is a supplement composition for enhancing DNA repair process, comprising effective amounts of a carotenoid compound; a nicotinamide compound; a zinc compound; inositol hexaphosphate; water extract of *uncaria tomentosa*; trans-resveratrol; extract of *arabidosis thaliana*; extract of cauliflower; and extract of *artemisia* plants.

20 Claims, No Drawings

SUPPLEMENT COMPOSITION FOR SUPPORTING DNA REPAIR AND METHOD OF USE

CROSS REFERENCE TO RELATED APPLICATION

This application claims the benefit under 35 USC 119(e) provisional patent application Ser. No. 61/534,637, filed Sep. 14, 2011, which is hereby incorporated by reference in its entirety.

FIELD OF THE INVENTION

The present invention relates to improved dietary supplement compositions for supporting DNA repair in both nucleus and mitochondria, and the method of use.

BACKGROUND OF THE INVENTION

DNA repair is a process constantly operating in cells. It is essential to survival because it protects the genome from damage and harmful mutations. In human cells, both normal metabolic activities and environmental factors can cause DNA damages, resulting in as many as 500,000 individual molecular lesions per cell per day. These lesions cause structural damage to the DNA molecule, and can dramatically alter the cell's way of reading the information encoded in its genes. Consequently, the DNA repair process must be constantly operating, to correct rapidly any damage in the DNA structures.

As cells age, however, the rate of DNA repair decreases until it can no longer keep up with ongoing DNA damage. The cell then suffers one of three possible fates: an irreversible state of dormancy, known as senescence; apoptosis or programmed cell death; carcinogenesis, or the formation of cancer. Most cells in the body first become senescent. Then, after irreparable DNA damage, apoptosis occurs. In this case, apoptosis functions as a "last resort" mechanism to prevent a cell from becoming carcinogenic and endangering the organism. Many genes that were initially shown to influence lifespan have turned out to be involved in DNA damage repair and protection.

Therefore, it is desirable to provide a dietary supplement composition that supports DNA repair processes in both nucleus and mitochondria, supports repair of DNA strand breaks and crosslinks, and supports arresting of the cell cycle to extend the time for DNA repair within the cell.

SUMMARY OF THE INVENTION

A supplement composition for enhancing DNA repair process, comprising effective amounts of a carotenoid compound; a nicotinamide compound; a zinc compound; inositol hexaphosphate; water extract of *uncaria tomentosa*; trans-resveratrol; extract of *arabidosis thaliana*; extract of cauliflower; and extract of *artemisia* plants.

Further a method for enhancing DNA repair process comprises orally administering a supplement composition to a person daily, said composition comprising in one dosage: from about 2,500 IU to about 10,000 IU of beta-carotene, from about 75 mg to about 500 mg of niacinamide, from about 5 mg to about 20 mg of zinc citrate, from about 250 mg to about 400 mg of inositol hexaphosphate, from about 100 mg to about 175 mg of water extract of *uncaria tomentosa*; from about 175 mg to about 200 mg of trans-resveratrol, from about 5 mg to about 8 mg of extract of arabidosis thaliana; from about 25 mg to about 35 mg of extract of cauliflower; and from about 20 mg to about 30 mg of extract of *artemisia* plants.

DETAILED DESCRIPTION OF THE INVENTION

In one aspect, the present invention provides dietary supplement compositions for supporting repair of DNA damages in both nucleus and mitochondria. In some embodiments, supplement compositions comprise a carotenoid compound, a nicotinamide compound, a zinc compound, inositol hexaphosphate, trans-resveratrol, water extract of *uncaria tomentosa*, extract of *arabidosis thaliana*, cauliflower extract, and extract of *artemisia* plants, and pharmaceutically acceptable medium or excipients.

The properties and functionalities of each individual component are described in detail hereinafter. In combination, the components of the supplement compositions achieve a synergistic effect in improvement of resistance to DNA damage by supporting or enhancing repair of naturally occurring DNA damages, which includes single and double strand breaks repair in nucleus, cross link damage repair in the nucleus, and base excision repair in mitochondrial DNA. The supplement compositions further have the effect of supporting arresting or slowing the cell cycle, which extend the time for DNA repair within the cell, without disrupting the normal cell function. This ultimately supports maintenance of an individual's health and reduces the likelihood of developing aging related disorders. Unless defined otherwise, all technical and scientific terms used herein have the same meaning as commonly understood by one having ordinary skills in the art to which the invention belongs.

Carotenoids such as beta carotene, sometimes called provitamin A, are water-soluble precursors which are converted to vitamin A by the body. Lycopene, lutein, and zeaxanthin are other carotenoids commonly found in food. The exact mechanism of action of carotenoids such as beta carotene is not fully understood but it is commonly accepted scientifically that one primary mechanism is to scavenge oxygen derived free radicals produced either as by-products of metabolism or from exogenous environmental exposures. As free radicals scavenger, carotenoids can be expected to reduce or protect against the chemical damage induced in DNA, RNA and protein of cells by toxic environmental exposures or endogenous cellular metabolic errors that ultimately can result in a disease state.

The carotenoid compound, as used herein, includes carotenoids, such as alpha carotene, beta carotene, gamma carotene, lycopene or combination thereof. Preferably, beta-carotene is used in the supplement composition, because beta-carotene is a carotenoid that is more efficiently converted to retinol than other carotenoids. In some embodiments, the supplement composition comprises beta-carotene, preferably in an amount ranging from about 2,500 to about 10,000 international unit (IU) in one dosage. In one example, the supplement composition comprises about 5,000 IU of beta-carotene in one dosage.

Herein, one dosage is also referred to as one serving. If the supplement composition is provided in the form of tablet, one dosage can be either one tablet, or more tablets. For example, 5,000 IU of beta-carotene in one dosage can be provided in one tablet or in two tablets. The size and number of tablets may depend on the manufacturability, which may further depend on the properties of the components and the pharmaceutically acceptable excipients used therein.

Nicotinamide and its metabolic equivalent nicotinic acid (niacin, vitamin $B_3$) or even tryptophane which is the synthetic precursor to niacin, is the main precursor for the formation and maintenance of the cellular pool of nicotinamide adenine dinucleotide (NAD). NAD is essential for cellular ATP production and maintenance of cell's redox potential, and it is also the substrate for the DNA repair enzyme, poly ADP-ribosyl transferase (ADPRT). Niacin deprivation decreases the NAD pool significantly both in tissue culture cells, animal systems and humans. It has been reported that NAD depleted cells have an increased sensitivity to DNA damage, and the levels of poly(ADP-ribose) production in cultured cells or in rat liver are significantly lower after mild nicotinamide deficiency. It has also been reported that when niacin was given as a supplement to ordinary nutrition (namely above known dietary levels), the NAD pool increased and the cells were less sensitive to oxygen radicals. Therefore, the primary mechanism of action of nicotinamide/niacin differs from carotenoids in that the cell's potential for energy metabolism is increased by amplifying NAD and ATP pool supplies, which in turn is useful to cells, tissues and organs to reduce DNA damage, enhance DNA repair (by poly ADP-ribosylation) and stimulate immune function.

The nicotinamide compound, as used herein, includes nicotinamide, niacin, tryptophane, NAD (nicotinamide-adenine dinucleotide), NADH (reduced form of NAD), NADP (NAD phosphate), NADPH (reduced form of NADP) or combination thereof. In some embodiments of the present invention, the supplement composition comprises nicotinamide in an amount ranging from about 125 mg to about 500 mg in one dosage. In one example, the supplement composition comprises about 250 mg of nicotinamide in one dosage.

Zinc differs from carotenoids and nicotinamide with regard to its mechanism of action in that it influences disease development and immune function by being an essential co-factor in several enzyme functions involving replication, DNA repair and antioxidant defense of cells. Zinc is required for cell replication and DNA polymerase activity. There are two zinc fingers in the DNA binding domain of the ADPRT gene and other DNA repair proteins which contain cysteine residues, and if these cysteine residues are oxidized at their thiol constituents, they would prevent DNA binding and participation in DNA repair.

The zinc compound, as used herein, includes an appropriate source of zinc for administration to humans and/or animals, for example, one or more zinc salts, such as zinc citrate, halides, nitrates, sulfates, oxides or acetates, or amino acids such as methionine or aspartate, dipeptides, or gluconates. In some embodiments, the supplement composition comprises zinc citrate, preferably in an amount ranging from about 5 mg to about 20 mg in one dosage. In one example, the composition comprises about 10 mg of zinc citrate in one dosage.

Resveratrol is a unique compound produced by the skins of grapes, grapevines and other plants and their roots in response to environmental stresses. It exists as two geometric isomers, cis-(Z) and trans-(E), and the trans-form can undergo isomerisation to the cis-form when exposed to ultraviolet irradiation. Trans-resveratrol in the powder form was found to be stable under the conditions of 75% humidity and 40° C. in the presence of air. Resveratrol content also is stable in the skins of grapes and pomace taken after fermentation and stored for a long period. Resveratrol has been reported having potent antioxidant activity and having the ability to inhibit platelet aggregation. It is believed that resveratrol plays an important role in the repair and maintenance of DNA strands. It has also been found that resveratrol is able to block all three mechanisms of cancer formation by helping the body inhibit tumor initiation, promotion and progression. Resveratrol has been used recently for caloric mimic therapy. In some embodiments, the supplement composition comprises trans-resveratrol, preferably in an amount ranging from about 175 mg to about 200 mg in one dosage. In one example, the composition comprises about 187 mg of trans-resveratrol in one dosage.

The Uncaria species includes *tomentosa, guianensis, pteropoda, homomalla, perrottetii,* or *rhynchopylla*. The bark or roots of *uncaria tomentosa* has been used as herbal medicine for many years. *Uncaria tomentosa* contains alkaloids such as mitraphylline, isomitraphylline, corynoxeine, isocorynoxeine, rhynchophylline, isorhynchophylline, dihydrocorynantheine, isopteropodine, pteropodine, uncarines C, D, E, F, harman, lyaloside, 5(S)-5-carboxystritosidine, 3,4-dehydro-5(S)-5-carboxystrictosidine; iridoids such as 7-deoxy loganic acid; 27-nor-triterpene glycosides such as tomentosides A, B; and organic acids such as quinic acid and caffeic acid. Water extract from the bark of *uncaria tomentosa* contains carboxy alkyl esters. It has been reported that water extract of uncaria *tomentosa* has repairing activity on human DNA damage and effect in enhancing natural occurring DNA repair.

The supplement compositions of the present invention comprise water extract of *uncaria tomentosa* for DNA repair. In some embodiments, the supplement composition comprises a water extract of *uncaria tomentosa* that contains 4 to 15% of carboxy alkyl esters, in an amount ranging from about 100 mg to about 175 mg in one dosage. In one example, the supplement composition comprises about 138 mg of water extract of *uncaria tomentosa* in one dosage.

Inositol hexaphosphate, also called inositol hexakisphosphate, phytic acid, is found within the hulls of nuts, seeds, and grains. In animal cells, myoinositol polyphosphates are ubiquitous, and myoinositol hexakisphosphate (one of the stereoisomers) is the most abundant, with its concentration ranging from 10 to 100 μM in mammalian cells, depending on cell type and developmental stage. Recent studies have suggested an intracellular role for inositol hexaphosphate as a cofactor in DNA repair by nonhomologous end-joining. (Hanakahi L A, et al., "Binding of inositol phosphate to DNA-PK and stimulation of double-strand break repair", *Cell* 102 (6): 721-729, (2000). Interstrand crosslinks are an extremely toxic class of DNA damage incurred during normal metabolism or cancer chemotherapy. Interstrand crosslinks covalently tether both strands of duplex DNA, preventing strand unwinding that is essential for polymerase access. It has been reported that inositol hexaphosphate involves in repair of crosslink DNA damage.

In the present invention, inositol hexaphosphate is used as a crosslink DNA damage repair compound. In some embodiments, the supplement composition comprises inositol hexaphosphate in an amount ranging from about 250 mg to about 400 mg in one dosage. In one example, the supplement composition comprises about 325 mg of inositol hexaphosphate in one dosage.

The extract of *arabidopsis thaliana* contains a DNA repair enzyme, 8-oxoguanine glucosylase. 8-Oxoguanine glycosylase, also known as OGG1, is a DNA glycosylase enzyme. It is involved in base excision repair, playing an important role in repairing the oxydative 8-oxoguanine damages in both nucleus and mitochondrial DNA.

The supplement composition of the present invention comprises the extract of *arabidopsis thaliana* for mitochondrial DNA base excision repair through its content of 8-oxoguanine DNA glucosylase. In some embodiments of the present invention, the supplement composition comprises extract of *arabidopsis thaliana* in an amount ranging from about 5 mg to about 8 mg in one dosage. In one embodiment, the supplement composition comprises about 6.5 mg of *arabidopsis thaliana* extract in one dosage.

Cauliflower contains several phytochemicals beneficial to human health. These include sulforaphane and other glucosinolates, carotenoids, and indole-3-carbinol which is a chemical that enhances DNA repair and acts as an estrogen antagonist, slowing the growth of cancer cells. In some embodiments of the present invention, the supplement composition comprises an extract of cauliflower, in an amount ranging from about 25 mg to about 35 mg in one dosage. In one embodiment, the supplement composition comprises about 30 mg of extract of cauliflower in one dosage.

*Artemisia* plants, such as *artemisia asiatica*, contains eupatilin, which is a O-methylated flavone, a type of flavonoids. It has been found that eupatilin derived from *artemisia* plants induces cell cycle arrest in ras-transformed human mammary epithelial cells (Kim D H, et al. *Biochem Pharmacol.* 2004, Sep. 15; 68(6):1081-7).

The extract of *artemisia* plants is used in the supplement composition of the present invention for inducing cell cycle arrest to extend the time for DNA repair within the cell. In some embodiments, the supplement composition comprises extract of *artemisia* plants in an amount ranging from about 20 mg to about 30 mg in one dosage. In one embodiment, the supplement composition comprises about 25 mg of extract of *artemisia* plants in one dosage.

All above described active components used in the illustrative, or preferred embodiments such as beta carotene, nicotinamide, zinc citrate, trans-resveratrol, inositol hexaphosphate, arabidosis thaliana extract, cauliflower extract, and extract of *artemisia* plants are commercially available. Example 1 illustrates an exemplary supplement composition of the present invention.

As convenient forms of dietary supplement, the supplement compositions described above can be provided in the form of tablet, capsule, or liquid. When other dosage forms are used, the amounts of the active components in one dosage or serving remain the same.

The supplement compositions can be formulated as a tablet or a capsule, containing pharmaceutically acceptable medium or excipients, according to methods and procedures well known in the art. As used herein, "excipients" means substances that are of little or no therapeutic value, but useful in the manufacture and compounding of various pharmaceutical preparations, which form the medium of the supplement compositions. The substances may include coloring, flavoring, and diluting agents, emulsifying and suspending agents, ointment bases, pharmaceutical solvents, antioxidants and preservatives for the product, and miscellaneous agents. Suitable excipients are described in Remington's Pharmaceutical Sciences, Mack Publishing Company, a standard reference text in this field, which is incorporated herein by reference in its entirety.

As used herein, "diluting agents" are inert substances added to increase the bulk of the formulation to make a tablet a practical size for compression. Commonly used diluting agents include calcium phosphate, calcium sulfate, lactose, kaolin, mannitol, sodium chloride, dry starch, powdered sugar, silica, and other suitable materials. As used herein, "binders" are agents used to impart cohesive qualities to the powdered material. Binders insure the tablet remaining intact after compression, as well as improving the free-flowing qualities by the formulation of granules of desired hardness and size. Materials commonly used as binders include starch; gelatin; sugars, such as sucrose, glucose, dextrose, molasses, and lactose; natural and synthetic gums, such as acacia, sodium alginate, extract of Irish moss, panwar gum, ghatti gum, mucilage of isapol husks, carboxymethylcellulose, methylcellulose, polyvinylpyrrolidone, Veegum, microcrystalline cellulose, microcrystalline dextrose, amylose, and larch arabogalactan, and other suitable materials. In one embodiment, the pharmaceutically acceptable medium includes dicalcium phosphate, microcrystalline cellulose, croscarmellose sodium, stearic acid, magnesium stearate, silica, and pharmaceutical glaze.

In another aspect, the present invention provides the method of using the supplement compositions described above as a dietary supplement to individuals, particularly those in need thereof. Preferably, the supplement composition is orally administered one or more times daily, more preferably one or twice a day. In one embodiment, the supplemental composition is orally administered twice a day, once in the morning and once in the evening; and each serving, or one dosage, includes from about 2,500 IU to about 10,000 IU of beta-carotene, from about 75 mg to about 500 mg of niacinamide, from about 5 mg to about 20 mg of zinc citrate, from about 250 mg to about 400 mg of inositol hexaphosphate, from about 100 mg to about 175 mg of water extract of *uncaria tomentosa*; from about 175 mg to about 200 mg of trans-resveratrol, from about 5 mg to about 8 mg of extract of arabidosis thaliana; from about 25 mg to about 35 mg of extract of cauliflower; and from about 20 mg to about 30 mg of extract of *artemisia* plants.

The supplement compositions of the present invention support multifunctional DNA repairs, including repairs of single and double strand breaks and interstrand crosslinks in the nucleus, and base excision repair in mitochondrial DNA. The supplement compositions further support arresting of the cell cycle, which extend the time for DNA repair within the cell. These effects ultimately improve an individual's resistance to DNA damage and reduce the likelihood of developing aging related disorders. The supplement compositions of the present invention are particularly suitable for those having poor genetic predisposition with regard to DNA repair, and those having early indication of disorders related to DNA damages.

Furthermore, the supplement compositions of the present invention can also be used in conjunction with other dietary supplements, such as multiple vitamins and other suitable supplements. In one example, the supplement compositions of the present invention can be used together with a supplement system described in a co-pending patent application entitled "Dietary Supplement System for Multifunctional Anti-Aging Management and Method of Use". This supplement system includes two compositions for oral administration in the morning and evening, respectively. The use of the present composition in addition to said supplement system further enhances the effect in DNA repair, particularly suitable for those in need thereof.

The following examples are illustrative of the invention and are in no way to be interpreted as limiting the scope of the invention, as defined in the claims.

Example 1

A composition of the following formulation was prepared in tablet form including pharmaceutically acceptable excipients, by methods known to those of ordinary skill in the art:

TABLE 1

Supplement Composition

| Contents | Amount Per Serving |
|---|---|
| Beta-carotene | 5,000 IU |
| Niacinamide | 150 mg |
| Zinc citrate | 10 mg |
| Inositol hexaphosphate | 325 mg |
| Water extract of uncaria tomentosa containing 4 to 15% of carboxy alkyl esters | 138 mg |
| Trans-resveratrol | 187 mg |
| Extract of arabidosis thaliana | 6.5 mg |
| Extract of cauliflower | 30 mg |
| Extract of artemisia plants | 25 mg |

Other ingredients include: dicalcium phosphate, microcrystalline cellulose, croscarmellose sodium, stearic acid, magnesium stearate, silica, and pharmaceutical glaze. In the example, the tablet has a weight from about 700 mg to about 900 mg.

Each patent, patent application, publication, text and literature article or report cited or indicated herein is hereby expressly incorporated by reference in its entirety.

While the invention has been disclosed in connection with certain preferred embodiments, this should not be taken as a limitation to all of the provided details. Modifications and variations of the described embodiments may be made without departing from the spirit and scope of the invention, and other embodiments should be understood to be encompassed in the present disclosure as would be understood by those of ordinary skill in the art.

What is claimed is:

1. A method for enhancing DNA repair processes in a person in need thereof comprising orally administering a supplement composition to the person daily, said composition comprising in one dosage: from about 2,500 IU to about 10,000 IU of beta-carotene, from about 75 mg to about 500 mg of niacinamide, from about 5 mg to about 20 mg of zinc citrate, from about 250 mg to about 400 mg of inositol hexaphosphate, from about 100 mg to about 175 mg of a water extract of Uncaria tomentosa; from about 175 mg to about 200 mg of trans-resveratrol, from about 5 mg to about 8 mg of an extract of Arabidopsis thaliana; from about 25 mg to about 35 mg of an extract of cauliflower; and from about 20 mg to about 30 mg of an extract of Artemisia asiatica.

2. The method of claim 1 wherein the DNA repair process corrects DNA damage selected from the group consisting of single stranded DNA breaks, double stranded DNA breaks, cross-link damage, and base excision repair.

3. The method of claim 1 wherein the beta carotene is present in an amount of 5000 IU.

4. The method of claim 1 wherein the supplement composition is in the form of a tablet, a capsule, or a liquid.

5. The method of claim 1 wherein the extract of Uncaria tormentosa contains 4% to 15% carboxy alkyl esters.

6. The method of claim 1 wherein the supplement composition further comprises 8-oxoguanine glucosylase.

7. The method of claim 1 wherein the supplement composition further comprises a pharmaceutically acceptable medium.

8. The method of claim 7 wherein the pharmaceutically acceptable medium is selected from the group consisting of coloring, flavoring, diluting agents, emulsifying agents, suspending agents, ointment bases, pharmaceutical solvents, antioxidants and preservatives.

9. The method of claim 1 further comprising administering the supplement composition in conjunction with a dietary supplement.

10. The method of claim 1 wherein the supplement further comprises a diluting agent.

11. The method of claim 10 further comprising administering the supplement composition in conjunction with a dietary supplement.

12. The method of claim 10 wherein the diluting agent comprises calcium phosphate, calcium sulfate, lactose, kaolin, mannitol, sodium chloride, dry starch, powdered sugar, silica, or combinations thereof.

13. The method of claim 1 wherein the supplement composition further comprises a binder.

14. The method of claim 13 wherein the binder further comprises starch; gelatin; sugars, such as sucrose, glucose, dextrose, molasses, and lactose; natural and synthetic gums, such as acacia, sodium alginate, extract of Irish moss, panwar gum, ghatti gum, mucilage of isapol husks, carboxymethylcellulose, methylcellulose, polyvinylpyrrolidone, Veegum, microcrystalline cellulose, microcrystalline dextrose, amylose, and larch arabogalactan.

15. The method of claim 14 further comprising administering the supplement composition in conjunction with a dietary supplement.

16. The method of claim 7 wherein the pharmaceutically acceptable medium comprises dicalcium phosphate, microcrystalline cellulose, croscarmellose sodium, stearic acid, magnesium stearate, silica, and pharmaceutical glaze.

17. The method of claim 1 wherein administration of the supplement composition occurs twice daily.

18. The method of claim 17 further comprising administering the supplement composition in conjunction with a dietary supplement.

19. The method of claim 1 wherein the administration of the supplement composition is to a person having early indication of disorders related to DNA damages.

20. The method of claim 19 further comprising administering the supplement composition in conjunction with a dietary supplement.

* * * * *